(12) United States Patent
Sharma et al.

(10) Patent No.: US 6,720,138 B2
(45) Date of Patent: Apr. 13, 2004

(54) METHOD OF PREPARING A STANDARD DIAGNOSTIC GENE TRANSCRIPT PATTERN

(75) Inventors: Praveen Sharma, Oslo (NO); Anders Lönneborg, Aas (NO)

(73) Assignee: Diagenic AS, Oslo (NO)

( * ) Notice: Subject to any disclaimer, the term of this patent is extended or adjusted under 35 U.S.C. 154(b) by 0 days.

(21) Appl. No.: 09/429,003

(22) Filed: Oct. 29, 1999

(65) Prior Publication Data

US 2002/0022222 A1 Feb. 21, 2002

Related U.S. Application Data

(63) Continuation of application No. PCT/GB98/01261, filed on Apr. 30, 1998.

(30) Foreign Application Priority Data

Apr. 30, 1997 (NO) ................................................ 972006

(51) Int. Cl.[7] .................................................. C12Q 1/68
(52) U.S. Cl. ........................ 435/6; 435/91.2; 536/24.3; 536/23.1; 204/450
(58) Field of Search .................. 435/91.2, 6; 536/24.3, 536/23.1; 204/450

(56) References Cited

U.S. PATENT DOCUMENTS

| | | | |
|---|---|---|---|
| 4,981,783 A | 1/1991 | Augenlicht | |
| 5,545,531 A | 8/1996 | Rava | |
| 5,633,137 A | 5/1997 | Paul | |
| 5,677,125 A | 10/1997 | Holt | |
| 5,800,992 A | 9/1998 | Fodor | |
| 5,830,645 A * | 11/1998 | Pinkel et al. | 435/6 |
| 5,871,928 A | 2/1999 | Fodor | |
| 5,874,219 A | 2/1999 | Rava | |
| 5,925,525 A | 7/1999 | Fodor | |
| 5,994,076 A | 11/1999 | Chenchik | |
| 6,004,755 A | 12/1999 | Wang | |
| 6,040,138 A | 3/2000 | Lockhart | |
| 6,190,857 B1 * | 2/2001 | Ralph et al. | 435/4 |

FOREIGN PATENT DOCUMENTS

| | | |
|---|---|---|
| EP | 0 408 918 | 1/1991 |
| EP | 0 534 640 | 3/1993 |
| GB | 2260811 | 4/1993 |
| WO | WO 93/18143 | 9/1993 |
| WO | WO 95 20681 | 8/1995 |
| WO | WO 97/22720 | 6/1997 |
| WO | WO 97/27317 | 7/1997 |
| WO | WO 97/29212 | 8/1997 |
| WO | WO 98/08083 | 2/1998 |
| WO | WO 99/06831 | 2/1999 |
| WO | WO 99/44062 | 9/1999 |
| WO | WO 99/49083 | 9/1999 |
| WO | WO 00/04187 | 1/2000 |
| WO | WO 00/14281 | 3/2000 |
| WO | WO 00/22168 | 4/2000 |
| WO | WO 00/22172 | 4/2000 |
| WO | WO 00/24940 | 5/2000 |
| WO | WO 00/26412 | 5/2000 |

OTHER PUBLICATIONS

US 6,066,453, 5/2000, Pinkel (withdrawn)
Sato et al. Acta Neurol. Scand 1995:91:165–168.*
Buckland et al. Molecular Brain Research 18(1993)316–320.*
Zhi–Xin et al. (Zhongguo Zhongliu Linchuang (1996) vol. 23, No. 4, pp. 243–246).*
Ditkoff et al. 1996. Surgery. 120(6): 959–965.*
Graber et al. Isolation of Differentially Expressed Genes in Carcinoma of the Esophagus. Annals of Surgical Oncology. 1(2): 192–197 (1996).*
Wadhwa et al. An Effective Elimination of False Positives Isolated from Differential Display of mRNAs. Molecular Biotechnology, 6: 213–217 (1996).*
Stratagene Catalog. 1988. p. 9.*
Enderlin et al, *FEBS Letters*, 412:629–632 (1997).
Schena et al, *Proc. Natl. Acad. Sci., USA*, 93:10614–10619 (1996).
Lonneborg et al, PCR Methods and Applications: Construction of Subtractive cDNA Library Using Magnetic Beads and PCR,. Cold Spring Harbor Laboratory, pp. 4:S168–S176 (1995).
Zhi–Xin et al, "Significance of IL–2R mRNA Expression in Patients with Lung Cancer", pp. 243–246 (Apr. 23, 1996) (Abstract).
Fujioka, *ACTA Hepatol. Jpn.*, 34(12):940–949 (1993) (Abstract).
Schena, *BioEssays*, 18(5):427–431 (1996).
Knöll et al, *BioChem. and Biophys. Res. Comm.*, 221:402–407 (1996), Article No. 0608.
Jonas et al, *Gut*, 39:717–721 (1996).
Krüger et al, *J. Cancer Res. Clin. Oncol.*, 122:679–686 (1996).
Shalon et al, *Genome Research*, 6:639–645 (1996).
Understanding the GEM Solution: Building a GEM Library, www.synteni.com/gemsol1.htm (1997).
Understanding the GEM Solution: Using Gene Expression Micro–Arrays, www.synteni.com/gemsol2.htm (1997).
Understanding the GEM Solution: Using Gene Expression Micro–Arrays, www.synteni.com/gemsol3.htm (1997).
Sample GEM Data, www.synteni.com/sample.htm (1997).
Schena et al, *Science*, 270(5235) :467–470 (1995).
Heller et al, *Proc. Natl. Acad. Sci. USA*, 94:2150–2155 (1997).

* cited by examiner

*Primary Examiner*—W. Gary Jones
*Assistant Examiner*—Juliet C. Switzer
(74) *Attorney, Agent, or Firm*—Sughrue Mion, PLLC (57) ABSTRACT

A method for preparing a gene transcript pattern probe kit characteristic of a disease or condition or a stage thereof in a prokaryotic or eukaryotic organism using mRNA which is differentially expressed in the disease or condition or stage as probes, methods of diagnosis using the method and kits for performing the same are disclosed.

13 Claims, 3 Drawing Sheets

SEQUENCE LISTING

```
<160> NUMBER OF SEQ ID NOS:  8

<210> SEQ ID NO 1
<211> LENGTH: 15
<212> TYPE: DNA
<213> ORGANISM: synthetic construct

<400> SEQUENCE: 1
gacgatgagt ccgac                                                    15

<210> SEQ ID NO 2
<211> LENGTH: 14
<212> TYPE: DNA
<213> ORGANISM: synthetic construct

<400> SEQUENCE: 2
cggtcaggac tcat                                                     14
```

-continued

<210> SEQ ID NO 3
<211> LENGTH: 17
<212> TYPE: DNA
<213> ORGANISM: synthetic construct

<400> SEQUENCE: 3
ctcgtagact gcgtacc                                                  17

<210> SEQ ID NO 4
<211> LENGTH: 13
<212> TYPE: DNA
<213> ORGANISM: synthetic construct

<400> SEQUENCE: 4
taggtacgca gtc                                                      13

<210> SEQ ID NO 5
<211> LENGTH: 21
<212> TYPE: DNA
<213> ORGANISM: synthetic construct

<400> SEQUENCE: 5
ctcgtagact gcgtacctaa t                                             21

<210> SEQ ID NO 6
<211> LENGTH: 19
<212> TYPE: DNA
<213> ORGANISM: synthetic construct

<400> SEQUENCE: 6
gacgatgagt cctgaccga                                                19

<210> SEQ ID NO 7
<211> LENGTH: 17
<212> TYPE: DNA
<213> ORGANISM: synthetic construct
<220> FEATURE:
<221> NAME/KEY: modified_base
<222> LOCATION: (16)..(17)
<223> OTHER INFORMATION: n at positions 16 and 17 is a, t, c or g

<400> SEQUENCE: 7
gactgcgtac ctaatnn                                                  17

<210> SEQ ID NO 8
<211> LENGTH: 18
<212> TYPE: DNA
<213> ORGANISM: synthetic construct
<220> FEATURE:
<221> NAME/KEY: modified_base
<222> LOCATION: (17)..(18)
<223> OTHER INFORMATION: n at positions 17 and 18 is a, t, c or g

<400> SEQUENCE: 8
gatgagtcct gaccgann                                                 18

METHOD OF PREPARING A STANDARD DIAGNOSTIC GENE TRANSCRIPT PATTERN

CROSS REFERENCE TO RELATED APPLICATIONS

This Application is a Continuation of PCT/GB98/01261 filed Apr. 30, 1998, which claims benefit of priority under 35 U.S.C. §365(c) and §120. The disclosure of PCT/GB98/01261 is incorporated herein by reference.

FIELD OF THE INVENTION

The present invention relates to methods of preparing standard diagnostic gene transcript patterns, probe kits for diagnosis and methods of diagnosis using such kits.

BACKGROUND OF THE INVENTION

There are numerous examples of diagnostic methods that include physical, anatomical and behavioural examination and/or biochemical, electrical, or electromagnetic studies and/or assays.

SUMMARY OF THE INVENTION

These diagnostic methods are well developed and are often efficient means to identify many pathological conditions. They are based on recent developments and research as well as on the observations, experience and empirical data recorded by health-workers concerned with diseases of human beings, other animals and plants for at least 6000 years.

Never before has the arsenal of diagnostic tools been greater than at present, but even so, incorrect diagnosis of ailments and other conditions is still commonplace.

New diseases and conditions are found that may be related to environmental changes or mutations or other alterations in both the active agents or organisms as well as in the organism that is exposed. In addition a number of old and new illegal substances used in sports and by drug addicts do not have appropriate diagnostic tests for their presence.

Several conditions are not easily identified with the available methods and/or the conclusive identification of a disease or condition may be reached too late for adequate corrective treatment.

Due to the extensive time often encountered in a complete diagnostic procedure, incorrect antibiotic therapy is often started prematurely, before a conclusive diagnosis is reached. This medical practice can aggravate the serious development of bacterial strains resistant to antibiotics.

Thus, even though a great number of differential diagnostic methods have been developed, there is still a considerable number of closely related conditions, or combinations of conditions that resist quick, safe and sure identification at low cost.

Furthermore, a number of diagnostic methods depend on the injection of foreign fluids or other kinds of transfer of diagnostic aids onto or into the organism under observation, or require biopsies. The removal of sample tissue from parts of the organisms often not easily accessible may also have a detrimental effect on the identification process and healing process itself.

It is known that certain diseases result in the elevated expression of different genes which may in some cases account for the pathogenicity of the disease or condition in question. Screening for the presence of a particular transcript as an indication of the presence of disease has thus been described (see for example Enderlin et al., FEBS Letters, (1997), 412, p629–632). Methods for quantifying the levels of different transcripts by binding to cDNA derived from gene libraries, or by sequencing and electronic comparison to other libraries has been described in for example Schena et al., (1996), PNAS USA, 93, p10614–10619; Schena et al., (1995), Science, 270, p467–470, Heller et al. (1997), PNAS USA, 94, p2150–2155 and International Patent Application No. WO95/20681.

However, a quick and simple method using the characteristic pattern of gene expression during disease or other conditions or stages thereof as a tool for diagnosis and/or prognosis, particularly a method which does not require any knowledge of the disease characteristics, the genes involved or their sequences has not been described.

It has now surprisingly been found that a simple method of diagnosis of a disease or condition or stage thereof may be performed by the preparation of a characteristic gene transcript pattern standard or fingerprint (standard diagnostic probe pattern) for that disease/condition followed by comparison of the transcript pattern of a patient or organism under study to that pattern. The standard is prepared by the identification of a number of specific and informative probes which serve as a set of markers for the disease or condition or stage thereof to be identified. These probes are bound to a solid support and then hybridized to mRNA, optionally reverse transcribed and/or amplified. The amount of the nucleic acid material which binds to the different probes is assessed and together forms the transcript pattern standard of that disease or condition or stage thereof.

Thus, in order to identify diseases, malaises or other conditions caused by other organisms, toxins, stress, ageing, environmental changes, etc, in human beings, animals, plants and all other living eukaryotic and prokaryotic organisms, a set of standard probe patterns of the amount of transcript from one or more informative genes relative to a standard may be developed, each such standard probe pattern being characteristic of one ailment or condition and/or stage of such ailment. These standard probe patterns are subsequently compared with a pattern of transcript levels, using the same probes, prepared from a recent sample of tissue or body fluid collected from a patient to be diagnosed, such patterns being specific to the present condition of the patient.

Usually the reaction to infections, toxins or deteriorations are accompanied by changes in the level of activity in several or many genes. These activity levels, that may either be relatively higher or lower, are together specific to the type of condition that is encountered. The normal activity and the altered activity may, to a large extent, be measured by the amount of specific transcript or mRNA that is present. Thus, standardised probes for analysis may be designed that have patterns of activity that are characteristic for each condition or combination of conditions that is to be identified or diagnosed. These standardised probes may be used to compare the standardised probe pattern with transcript patterns from samples of tissue or body fluids prepared in a similar way and obtained from a live patient or the organism to be studied.

In order to put the invention into practical use, two kinds of substantially similarly developed diagnostic probes must be available for comparison.

1. A standard diagnostic probe pattern (SDPP) that is characteristic of the suspected ailment, developed from one or more organisms having the condition or disease or stage thereof in question.

and

2. A patient specific probe pattern (PSPP) that is developed from a recently obtained sample of tissue or body fluid from a organism to be studied.

To apply the invention to a specific condition, the pattern of a SDPP characteristic of the suspect ailment or stage thereof must have been developed beforehand. In addition, a recent, well preserved sample of tissue or body fluid from the patient must be available to develop the PSPP, for comparison with one or several different SDPPs for the number of ailments and their different stages that is suspected.

To design and develop the pattern for SDPPs, characteristic for one ailment, known techniques of isolation of mRNA, construction and amplification of cDNA and selection through differential hybridisation and differential display may be used.

Selected informative mRNA or cDNA probes from one or more patients that have been conclusively diagnosed with the ailment in question are isolated and amplified. These SDPPs together will be used to compare if the PSPP is similar to the SDPP. Several such characteristic SDPPs may be developed to represent different stages of the same ailment.

The pattern of such standard probes for a great number of ailments and different stage of such ailments may be accumulated in databases and be made available to laboratories on request.

Thus, viewed from one aspect the present invention provides a method of preparing a gene transcript pattern probe kit for diagnosing or identifying a disease or condition or stage thereof in a prokaryotic or eukaryotic organism comprising at least the steps of:
  a) isolating mRNA from the tissue, cells or body fluid of a normal prokaryotic or eukaryotic organism (normal sample);
  b) isolating mRNA from the corresponding tissue, cells or body fluid of an organism of step a) having the disease or condition of interest or a stage thereof (diseased sample);
  c) separating the mRNA of steps a) and b), which may optionally be reverse transcribed to cDNA, by a non-sequence based separation technique;
  d) selecting two or more mRNA or cDNA species which are present at different levels in the normal and diseased samples;
  e) isolating the mRNA or cDNA species identified in step d);
  f) optionally reverse transcribing the mRNA of step d) or e) to cDNA, unless this has previously been performed in step c); and
  g) immobilizing the mRNA or cDNA probes of step e) or f) on one or more solid supports.

DETAILED DESCRIPTION OF THE INVENTION

As used herein the disease or condition may be any condition, ailment, disease or reaction that leads to the relative increase or decrease in the activity of informative genes of any or all eukaryotic or prokaryotic organisms regardless of whether these changes have been caused by the influence of bacteria, virus, prions, parasites, fungi, radiation, natural or artificial toxins, drugs or allergens, including mental conditions due to stress, neurosis, psychosis or deteriorations due to the ageing of the organism, and conditions or diseases of unknown cause.

Such diseases include those which result in metabolic or physiological changes, such as fever-associated diseases such as influenza or malaria. Other diseases which may be detected include for example yellow fever, sexually transmitted diseases such as gonorrhea, fibromyalgia, candida-related complex, cancer (for example of the stomach, lung, breast, prostate gland, bowel, skin etc), Alzheimer's disease, disease caused by retroviruses such as HIV, senile dementia, multiple schlerosis and Creutzfeldt-Jakob disease to mention a few.

The invention may also be used to identify patients with psychiatric or psychosomatic diseases such as schizophrenia and eating disorders. Of particular importance is the use of this method to detect diseases, or stages thereof, which are not readily detectable by known diagnostic methods, such as HIV which is generally not detectable using known techniques 1 to 4 months following infection. Conditions which may be identified include for example drug abuse, such as the use of narcotics, alcohol, steroids or performance enhancing drugs. The diagnostic method may be used alone as an alternative to other diagnostic techniques or in addition to such techniques. For example, methods of the invention may be used as an alternative or additive diagnostic measure to diagnosis using imaging techniques such as Magnetic Resonance Imagine (MRI), ultrasound imaging, nuclear imaging or X-ray imaging, for example in the identification and/or diagnosis of tumours.

"Stages" thereof refer to different stages of the disease or condition which may or may not exhibit particular physiological or metabolic changes, but does exhibit changes at the genetic level which may be detected as altered gene expression. It will be appreciated that during the course of a disease or condition the expression of different transcripts may vary. Thus at different stages, altered expression may not be exhibited for particular transcripts compared to "normal" samples. However, informative probes are selected from those transcripts which exhibit altered expression at one or more stages through the course of the disease and which together with information relating to the level of other transcripts can be used to provide a characteristic pattern which is indicative of a particular stage of the disease. Such informative probes may be identified by comparing the transcripts of normal samples with transcripts of diseased samples from one or more stages of the disease or condition, or by comparing different stages of the disease or condition to one another, according to the above described method.

As used herein the prokaryotic or eukaryotic organism may be any eukaryotic organisms such as human beings, other mammals and animals, birds, insects, fish and plants, and any prokaryotic organism such as a bacteria.

As used herein the "tissue" may be a tissue obtained during surgery, for example by biopsy, or by other means. "Cells" include cells isolated from tissues or body fluids or body waste or in the case of prokaryotic organisms, the organism itself. "Body fluids" include urine, blood, semen etc. It will however be appreciated that the method of preparing the standard transcription pattern and method of diagnosis of the invention is also applicable to use on living parts of eukaryotic organisms such as cell lines and organ cultures and explants.

"Normal" as used herein refers to organisms or samples which are used for comparative purposes. Preferably, these are "normal" in the sense that they do not exhibit any indication of, or are believed to have, any disease or condition that would affect gene expression, particularly in respect of the disease for which they are to be used as the standard. However, it will be appreciated that different stages of a disease or condition may be compared and in such cases, the "normal" sample corresponds to the earlier stage of the disease or condition. "Disease" samples and organisms include samples and organisms suffering from an ailment or particular condition and are those known to have, or which exhibit, the disease or condition or stage thereof under study.

"Complementary strands" is used in the conventional sense to refer to strands of DNA which are complementary at each base to the template cDNA from which they are derived. "cDNA" as referred to herein includes first strand cDNA produced by reverse transcription of RNA and complementary strands to the first strand cDNA, namely second strand cDNA.

"Different levels" of the nucleic acids species refers to quantitative or qualitative differences suggestive of differential expression. A "probe" may be one or more nucleic acid molecules which may be the same or different (ie. a mixture) but which as a whole are differentially expressed in the normal and diseased samples. When different stages of the disease/condition are investigated, differential expression of the transcripts corresponding to the probes should be exhibited either relative to an undiseased sample or relative to a different stage of the disease/condition. Generally such probes are cDNA reverse transcribed from mRNA, or its complementary strands, although the mRNA itself may also be used. This could for example be achieved using a DNA fragment as a template for the probe by insertion in a vector behind a T3 or similar promoter. It will be appreciated however that this nucleic acid material may be modified without affecting performance of the invention providing hybridization to sample nucleic acid molecules is still possible. Thus the nucleic acid molecules referred to herein, such as mRNA and cDNA, includes molecules which are modified (e.g. methylated) or which include modified or non-natural bases which may be used in the preparation of the cDNA or during amplification. Similar considerations apply to any nucleic acid molecules described herein. Thus for example, the transcripts, present in the samples, may be in the form of RNA or altered to modified forms of RNA and/or into modified or unmodified forms of DNA and/or in the form of, primers, antibodies or other molecules that recognize and bind to target probes, particularly by specific hybridisation to the target probes.

"Assessing" as used herein refers to both quantitative and qualitative assessment which may be determined in absolute or relative terms. The characteristic "pattern" created by this technique refers to information which for example may be represented in tabular or graphical form and conveys information about the signal associated with two or more probes.

As used herein, reference to "corresponding" tissues etc. refers to preferably the same tissue, cells or fluid, but also includes tissue, cells or fluid which are sufficiently similar for the purposes of preparing the standard. When used in reference to genes "corresponding" to the probes, this refers to genes which are related by sequence (which may be complementary) to the probes although the probes may reflect different splicing products of expression. Thus two separate probes may be developed for a single disease which are transcribed from the same gene but reflect different splicing events. However the use of probes which reflect altered gene expression of two or more distinct genes is preferred.

This invention relates to both a diagnostic principle and a method of identifying diseases, malaises and syndromes in any eukaryotic or prokaryotic organism as well as the associated method for the design and development of diagnostic probes to be used in the relative measurements necessary to reach specific diagnosis or to identify relevant conditions.

The invention is a quick and precise method for the diagnosis of any disease or condition that leads to alterations in the activity of genes in a pattern which is specific to any particular condition of the organism under observation.

The ability to design diagnostic standard probes for the identification of traditional conditions, that at present are hard to identify, as well as the ability to quickly adapt the design to prepare new probes for the identification of new conditions that may appear, as soon as they are identified, will therefore be of great value.

From the very early stages of diseases caused by infections, toxic substances, ageing or other conditions changing the quality of life of living eukaryotic organisms, the whole organism responds to the changed condition. The response occurs, throughout the organism, even if only a minor part of the organism appears to be affected. The response lasts until the condition is healed or until the death of the affected organism The advantages of the invention are of both primary and secondary nature. Samples of tissue or body fluids may be obtained from parts of the organism that are not affected by the condition under observation. One sample will suffice for a complete identification, thus great reductions in costs, time and inconvenience may result by avoiding hospitalization during the normal extensive range of diagnostic tests performed on human and other animal patients.

No foreign substances need be introduced onto or into the organism under observation in order to aid in the identification of the condition, thus the invention will reduce the risk of anaphylactic reactions to such induced diagnostic substances.

The invention has the potential to detect most diseases and syndromes of somatic, psycho-somatic and mental character as well as detecting deterioration due to ageing of the organism. In addition the method may be used to detect the organism's reactions to toxic substances, radiation, pesticides, antibiotics, drugs, allergens and combinations of several such conditions.

The invention will furthermore make it possible to detect diseases or undesirable conditions in an organism at very early stages, even years before other subjective or objective symptoms may appear.

Even in cases where the patient dies from a hitherto unidentified condition and the cause of death is not established until a forensic post-mortem examination has been performed, the principle will be of value. If, in the attempt to diagnose the patient prior to death, a series of patient specific probe patterns were developed, these probes may be used for the design of new standard probe patterns that may be used to diagnose later occurrences of similar conditions.

The analytical instruments and equipment necessary to make use of the invention is readily available in laboratories engaged in standard biochemical and bio-technological work.

To begin the preparation of the gene transcript pattern probe kit, mRNA is extracted from the tissues, cells or body fluid according to known techniques (see for example Sambrook et. al. (1989), Molecular Cloning: A laboratory manual, 2nd Ed., Cold Spring Harbor Laboratory Press, Cold Spring Harbor, N.Y.) from a normal individual or organism.

mRNA is also extracted, preferably from the same body part of a corresponding individual or organism which has the disease or condition for which the standard diagnostic pattern is to be created. Owing to the difficulties in working with RNA, the RNA is preferably reverse transcribed at this stage to form first strand cDNA, although this may be performed after separation and identification of transcripts of interest if cDNA probes are to be generated. Cloning of the cDNA or selection from, or using, a cDNA library is not however necessary in this or other methods of the invention.

Preferably, the complementary strands of the first strand cDNAs are synthesized, ie. second strand cDNAs, but this will depend on which strands are proposed to be used as the probes and the nature of the nucleic acid molecules in the sample to be probed during the diagnosis method. The second strand cDNA strands are preferably used to probe cDNA strands which have been produced by reverse transcription of the sample mRNA.

Preferably the cDNA strands are amplified by known amplification techniques such as the polymerase chain reaction (PCR) by the use of appropriate primers. Alternatively, the cDNA strands may be cloned with a vector, used to transform a bacteria such as *E. coli* which may then be grown to multiply the nucleic acid molecules. When the sequence of the cDNAs are not known, primers may be directed to regions of the nucleic acid molecules which have been introduced. Thus for example, as described in the Examples herein, adapters may be ligated to the cDNA molecules and primers directed to these portions for amplification of the cDNA molecules. Alternatively, in the case of eukaryotic samples, advantage may be taken of the polyA tail and cap of the RNA to prepare appropriate primers.

Separation of the normal and diseased sample mRNA or cDNA is performed separately on each sample by non-sequence based separation techniques which are any suitable techniques which allows discrimination between transcripts or their corresponding cDNAs without involving the use of sequence information of particular transcripts to discriminate between the different transcripts/cDNA. This does not however exclude the possibility of for example using probes carrying labels to produce signals on the transcripts if the probes are directed to sequences common on all or most of the transcripts which are not used for the purpose of discriminating transcripts. Thus conveniently, mRNA or cDNA may be separated by electrophoretic separation on an agarose or polyacrylamide gel or a similar gel appropriate for the separation of the nucleic acid molecules. Alternatively, the products may be separated by gas chromatography or HPLC or similar techniques. (Sequence based separation techniques, which are excluded, include for example capture with probes directed to different sequences by hybridization or sequencing itself.)

Such methods offer the advantage that probes to be used in the methods of the invention are identified and selected from the entire population of transcripts or cDNA since no selection is made on the basis of their sequence before separation, e.g. by hybridization to immobilized nucleic acid from control samples. Thus, the identification of the transcripts is not biased towards the selection of particular transcripts from a subset of total transcripts.

To allow comparison between the samples, separation of the transcripts/cDNA should be performed on the normal and diseased samples as simultaneously as possible, e.g. consecutive runs or on the same gel.

To identify the different transcripts or cDNA, it is necessary to identify a signal corresponding to each transcript/cDNA. Conveniently this may be achieved by the use of a radioactive or other label which may be incorporated during cDNA production or during amplification.

Appropriate labels are those which directly or indirectly allow detection or measurement of the presence of the transcripts/cDNA. Such labels include for example radiolabels, chemical labels, for example chromophores or fluorophores (e.g. dyes such as fluorescein and rhodamine), or reagents of high electron density such as ferritin, haemocyanin or colloidal gold. Alternatively, the label may be an enzyme, for example peroxidase or alkaline phosphatase, wherein the presence of the enzyme is visualized by its interaction with a suitable entity, for example a substrate. The label may also form part of a signalling pair wherein the other member of the pair is found on, or in close proximity to, the target probe to which the transcript/cDNA binds, for example, a fluorescent compound and a quench fluorescent substrate may be used. A label may also be provided on a different entity, such as an antibody, which recognizes a peptide moiety attached to the transcripts/cDNA, for example attached to a base used during synthesis or amplification.

A signal may be achieved by the introduction of a label before, during or after the separation step. Thus for example, a gel on which the transcripts have been separated could be probed with labelled polyT oligonucleotides, or cDNA could be probed with labelled polyA oligonucleotides or probed with labelled oligonucleotides directed to a sequence which is introduced by ligation and/or amplification. Alternatively, the presence of transcripts could be identified by other physical properties, such as their absorbance, if techniques such as gas chromatography or HPLC are employed for separation.

Depending on the technique used for separation, signals for different transcripts or their cDNA may overlap and not be fully resolved. Whilst probes may be produced which contain a mixture of transcripts or their cDNA (providing the mix as a whole exhibits differential expression in normal and diseased samples), optionally, the mixture of transcripts/cDNA may be extracted and subjected to repeated or alternative separation techniques to isolate a smaller population of transcripts/cDNAs which exhibits the altered expression.

Nucleic acid species exhibiting differential expression in normal versus diseased samples, or in at least one stage of said disease, are identified. This requires comparison between the signals produced by the normal and diseased samples. Transcripts/cDNAs of interest are those which are differentially expressed in the different samples as exhibited by different amounts of signal. This may correspond to a species present in the diseased sample and not in the normal sample or vice versa. In this way both gene expression which is turned on and gene expression which is turned off is reflected. This offers significant advantages over prior art methods in which altered gene expression is identified relative to normal samples (in which cDNA from normal libraries is used as the hybridization template to which sample mRNA is bound and the relative difference between "normal" and "diseased" samples are measured). The method of the invention thus can identify genes which are not constitutively expressed or are expressed only at very low levels in normal samples, but are activated in the disease/condition, or at least one stage thereof, in question.

Transcripts/cDNA which reflect a variation in the extent of expression may be used, but it is preferable to use those species which reflect marked differences, e.g. absence or presence of a transcript/cDNA.

Once identified, the mRNA or cDNA species (which may be a mixture of molecules having different sequences) are isolated. To prepare a standard diagnostic pattern, two or more species (probes) which reflect altered gene expression in at least one stage of said disease or condition may be isolated. Whilst in some cases only two probes may be sufficient to produce a standard diagnostic pattern for a particular condition or disease or stage thereof, it will be appreciated that increasing the number of probes will prevent the possibility of misdiagnosis by comparison to other diseases which could similarly alter the expression of the particular genes in question. Thus preferably between 2 and 1000 probe species are selected for isolation, especially preferably between 10 and 500, particularly preferably 50 and 100, for example 70 probe species. These probes reflect genes which have altered expression in the diseases or conditions in question, or particular stages thereof are considered "informative" for that particular disease in the organism under study and only those probes having this informative property are selected.

Isolation may be by selection of appropriate fractions if for example separation was performed on a column, or by physical removal from the separation matrix, for example excision of gel slices containing the nucleic acid species of interest. The nucleic acid molecules contained therein are then isolated and purified if necessary for the subsequent steps, preferably with amplification.

In instances in which the transcripts themselves have been separated and isolated, these may then be converted to cDNA, preferably with amplification.

The mRNA or cDNA probe species produced according to the above method are then each immobilized onto a solid support to produce the disease's or condition's probe kit or gene transcript pattern (or fingerprint) probe kit. Numerous solid supports suitable as immobilizing moieties for nucleic acid molecules are well known in the art and widely described in the literature and generally speaking, the solid support may be any of the well-known supports or matrices which are currently widely used or proposed for immobilization, separation etc. in chemical or biochemical procedures. Thus for example, the immobilizing moieties may take the form of particles, sheets, gels, filters, membranes, microfibre strips, tubes or plates, fibres or capillaries, made for example of a polymeric material e.g., agarose, cellulose, alginate, teflon, latex or polystyrene. Particulate materials, e.g. beads, are generally preferred. Conveniently, the immobilizing moiety may comprise magnetic particles, such as superparamagnetic particles.

Attachment of the nucleic acid molecules to the solid support may be performed directly or indirectly. For example if a filter is used, attachment may be performed by UV-induced crosslinking. Alternatively, attachment may be performed indirectly by the use of an attachment moiety carried on the nucleic acid molecules and/or solid support. Thus for example, a pair of affinity binding partners may be used, such as avidin, streptavidin or biotin, DNA or DNA binding protein (e.g. either the lac I repressor protein or the lac operator sequence to which it binds), antibodies (which may be mono- or polyclonal), antibody fragments or the epitopes or haptens of antibodies. In these cases, one partner of the binding pair is attached to (or is inherently part of) the solid support and the other partner is attached to (or is inherently part of) the nucleic acid molecules.

Attachment of appropriate functional groups to the solid support may be performed by methods well known in the art, which include for example, attachment through hydroxyl, carboxyl, aldehyde or amino groups which may be provided by treating the solid support to provide suitable surface coatings. Attachment of appropriate functional groups to the nucleic acid molecules of the invention may be performed by ligation or introduced during synthesis or amplification, for example using primers carrying an appropriate moiety, such as biotin or a particular sequence for capture.

The individual probes form modules of the kit and may be present on one or more solid supports. The solid support of the different modules are conveniently physically associated although the signals of each probe must be separately determinable. Thus for example, plates with multiple wells may be used as the solid support with different probes in the different wells, or regions of a solid support may comprise the different modules, for example the different mRNA or cDNA probes may be bound to a filter at discrete sites.

Thus in a preferred aspect the present invention provides a method of preparing a gene transcript pattern probe kit for diagnosing or identifying a disease or condition or stage thereof in a prokaryotic or eukaryotic organism comprising at least the steps of:

a) isolating mRNA from the tissue, cells or body fluid of a normal prokaryotic or eukaryotic organism (normal sample);

b) isolating mRNA from the corresponding tissue, cells or body fluid of an organism of step a) having the disease or condition of interest or a stage thereof (diseased sample);

c) reverse transcribing the mRNA of steps a) and b) to cDNA;

d) optionally amplifying said strands, optionally incorporating a label into said strands;

e) separating the cDNA of step d) by a non-sequence based separation technique;

f) selecting two or more cDNA species which are present at different levels in the normal and diseased samples;

g) isolating the cDNA species identified in step f); and h) immobilizing the cDNA probes of step g) on one or more solid supports.

The gene transcript pattern probe kits prepared according to the above method for diagnosing or identifying a particular disease/condition or stage thereof in a particular individual/organism or for preparing a standard diagnostic gene transcript pattern, form further aspects of the invention.

Thus viewed from a further aspect the present invention provides a gene transcript pattern probe kit for diagnosing, identifying or preparing a standard diagnostic gene transcript pattern of a disease or condition or stage thereof in a eukaryotic or prokaryotic organism comprising at least the following:

a) one or more solid supports carrying two or more probe species according to the invention corresponding to transcripts which reflect gene expression of one or more selected genes characteristic in the condition or disease or stage thereof in the organism under investigation.

Optionally the kit may also contain information relating to the signals generated by normal or diseased samples, standardizing materials, e.g. mRNA or cDNA from normal and/or diseased samples for comparative purposes, labels for incorporation into cDNA, adapters for introducing nucleic acid sequences for amplification purposes, primers for amplification and/or appropriate enzymes, buffers and solutions.

The use of such kits to prepare a standard diagnostic gene transcript pattern forms a further aspect of the invention.

In a yet further aspect, the present invention provides a method of preparing a standard diagnostic gene transcript pattern characteristic of a disease or condition or stage thereof in a prokaryotic or eukaryotic organism comprising at least the steps of:

a) isolating mRNA from the tissue, cells or body fluid of said organism having the disease or condition or stage thereof, which may optionally be reverse transcribed to cDNA, b) hybridizing the mRNA or cDNA of step a) to the mRNA or cDNA probes on a kit according to the invention specific for said disease or condition or stage thereof in an organism corresponding to the organism under investigation; and c) assessing the amount of mRNA or cDNA hybridizing to each of said probes on said solid support(s) to produce a characteristic pattern reflecting gene expression in the sample with the disease, condition or stage thereof of one or more selected genes corresponding to the probes.

To produce the standard diagnostic gene transcript pattern or fingerprint for a particular disease or condition or stage thereof, the above produced probe kit is used to probe mRNA or cDNA of a diseased sample to give a signal for hybridization to each particular probe species bound to the solid support, ie. the kit modules. A standard control gene transcript pattern may be prepared if desired using mRNA from a normal sample. Thus, total mRNA isolated in the same manner as described above, or its cDNA (depending on the complementarity of the probe species on the probe kit module) of a diseased sample (corresponding to the disease to which the probes are directed) (optionally also a normal sample) is hybridized under appropriate conditions to the probe species on the probe kit modules. When both samples are probed, this may be performed consecutively on the same probe kit modules, by simultaneously hydridizing to the modules of a corresponding probe kit.

To obtain an indication of the number of transcripts/cDNA molecules which become bound to the probe kit modules, the signal produced when the transcripts hybridize is detected (e.g. by detection of double stranded nucleic acid molecules or detection of the number of molecules which become bound, after removing unbound molecules, e.g. by washing). In the latter case, preferably labelled mRNA/cDNA molecules are used as the sample, for example by incorporating radiolabelled bases during reverse transcription, the preparation of complementary cDNA strands or amplification. The amount of signal is then assessed for each probe kit module. The assessment may be quantitative or qualitative and may be based on binding of a single transcript species to each probe, a combination of transcripts, or representative forms of the transcripts such as cDNA or modified nucleic acid molecules as described above. It will be appreciated that quantitative results will provide further information for the transcript fingerprint of the disease which is compiled. This data may be expressed as absolute values or may be determined relative to a particular standard or probe module result. The value of the signal from the normal sample may be subtracted from the signal from the disease sample, where the former is determined, although preferably results from test samples are compared to the unstandardized disease fingerprint which is produced.

Furthermore it will be appreciated that the standard diagnostic gene pattern transcript may be prepared using the results of one or more diseased and/or normal samples to identify probes for the probe kit, and one or more disease samples (and normal samples if used) may be used to perform the hybridization step to obtain the standard diagnostic gene transcript pattern.

The use of such kits and standard diagnostic gene transcript patterns for the purpose of identification or diagnosis of a particular disease or condition or stage thereof in a particular organism forms a further aspect of the invention.

Once a standard diagnostic fingerprint or pattern has been determined for a particular disease or condition using the selected probe species, this information can be used to identify the presence, absence or extent of that disease or condition in a different organism or individual.

Thus viewed from a further aspect the present invention provides a method of diagnosing or identifying a disease or condition or stage thereof in a prokaryotic or eukaryotic organism, comprising the steps of:

a) isolating mRNA from the tissue, cells or body fluid of said organism, which may optionally be reverse transcribed to cDNA;

b) hybridizing the mRNA or cDNA of step a) to a kit of the invention specific for said disease or condition or stage thereof in an organism corresponding to the organism under investigation;

c) assessing the amount of mRNA or cDNA hybridizing to each of said probes on said solid supports to produce a characteristic pattern reflecting gene expression of one or more selected genes corresponding to the probes;

d) comparing said pattern to a standard diagnostic pattern prepared according to the method of the invention using a sample from an organism corresponding to the organism under investigation having said disease or condition or stage thereof under investigation to determine the degree of correlation indicative of the presence of said disease or condition or a stage thereof in the organism under investigation.

The degree of correlation which is required to confirm the presence, absence or extent of a disease or condition necessarily takes into account the range of values which are obtained for normal and diseased samples. Although this can be established by obtaining standard deviations for several representative samples binding to the probes to develop the standard, it will be appreciated that single samples may be sufficient to generate the standard pattern to identify a disease if the test sample exhibits close enough correlation to that standard.

The diagnostic method may be used to identify, quantify or diagnose a disease, condition or ailment or its stage or progression, for example cancer in humans and bovine spongiform encephalopathy in cattle. The methods of the invention may also be used to monitor the condition/state of plants, for example to monitor the effects of pollution, or in the case of prokaryotic organisms, to monitor their state during such processes as fermentation or sewage processing.

Owing to the effects that certain exogenous factors or diseases exert on all parts of body, ie. the effects on gene expression are not isolated to the areas of apparent disease, and thus body parts distant from the site of interest, e.g. a tumour, may be analysed. Thus samples may be obtained for testing in a non-invasive manner, such as for example a body fluid, such as blood. Since samples may originate from different parts of the body which may exhibit some differences in their transcription products, samples used to prepare the standard and test samples should preferably be matched. In the diagnosis methods of the invention three different samples are concerned which could be derived from different sources. These are the samples used to prepare the probes, the disease sample used to prepare the standard diagnosis pattern and the test sample. Preferably all samples are derived from comparable sources, but especially preferably at least the disease sample used to prepare the standard pattern and the test sample are derived from a corresponding source.

The following examples are given by way of illustration only in which the Figures referred to are as follows:

EXAMPLES

Example 1
Diagnosis of Alzheimer Syndrome

A blood sample is collected from a patient suspected of suffering from the ailment. The sample is immediately preserved in liquid nitrogen to prevent degradation of the mRNA of the sample.

The sample is transferred for analysis, the mRNA is converted to cDNA, amplified by PCR (Polymerase Chain Reaction) and labelled with suitable radioactive nucleotides.

The labelled cDNA is hybridized to several diagnostic DNA probes that are immobilized on a filter.

The radioactive signals from the PSPP filter are quantified using an Instant Imager and the relative signal value from each of the different probes is determined.

The relative values from the different probes will together create a pattern that is specific for the patient's ailment, the PSPP.

This specific pattern for the patient is compared to the SDPPs characteristic of Alzheimer syndrome in different stages. If the patterns of the SDPP and the PSPP coincide, the ailment and its stage is diagnosed with great certainty.

If the patterns do not coincide, the ailment may be ruled out and the same PSPP may be compared manually or automatically to any number of available SDPPs until a match is found.

Example 2
Diagnosis of Senile Dementia

The patient specific sample is collected, preserved, the mRNA is converted to cDNA, amplified and labelled through the same procedure as described in Example 1.

The comparative hybridization is performed with a different set of SDPPs that have been developed to distinguish between different kinds and stages of senile dementia.

Example 3
Broad Spectrum Health Status

The patient specific sample is collected, preserved, the mRNA is converted to cDNA, amplified and labelled through the same procedure as described in Example 1.

Primers to detect a set of transcripts are used for labelling.

The labelled samples are separated through gel electrophoresis and all the DNA fragments are detected and quantified.

The resulting pattern specific to the patient PSPP is subsequently compared to SDPPs of a number of different diseases. For every mismatch encountered the associated ailment may be ruled out.

Example 4
Diagnosis of a Disease/Condition in Arabidopsis

The diagnosis may be divided in two steps:

Development of a reproducible expression pattern (fingerprint) typical for the disease/condition to be diagnosed.

Applying the developed method to a sample from an undiagnosed patient or organism and comparing the expression pattern to patterns developed for the disease/condition.

4.1 Development of a Reproducible Expression Pattern Typical for the Disease/Condition to be Diagnosed 4.1.1 Extraction of Total RNA from Leaves of Arabidopsis Samples of 15 g of leaves each from plants with a diagnosed disease and from healthy plants are collected and frozen immediately in liquid nitrogen. Each sample is divided into two aliquots.

The leaves from one of the two aliquots from each sample are ground with a mortal and pestle in liquid nitrogen to a fine powder. The second aliquot of each sample is stored at −70° C.

The ground leaves are immediately transferred to a 500 ml beaker with 150 ml grinding buffer (0.18M Tris-HCl, pH 8.2, 0.09M LiCl, 4.5 mM EDTA, 1% (w/v) Sodium dodecyl sulfate (SDS) plus 50 ml TLE-equilibrated phenol (TLE= 0.2M Tris-HCl, pH 8.2, 0.1M LiCl, 5 mM EDTA)).

The mixture is homogenized with a polytron for 2 min at moderate speed (setting 5–6). 50 ml chloroform is added and mixed into the homogenate using the Polytron. The slurry is poured into a centrifuge bottle and heated for 20 min at 50° C. This is then centrifuged for 20 min at 17 700×g, 4° C.

After centrifugation, as much of the aqueous layer as possible is removed without disturbing the interface and in a new centrifuge bottle this phase is mixed with 50 ml TLE-equilibrated phenol by shaking. 50 ml chloroform is then added and the bottle is shaken vigorously and then centrifuged at 17 700×g, 15 min, 4° C.

After centrifugation, the aqueous phase is removed and reextracted with TLE-equilibrated phenol until no interface is obtained. The aqueous phase is extracted once with chloroform.

The aqueous phase is transferred to a clean centrifuge bottle and 8M LiCl is added to a final concentration of 2M LiCl. RNA is precipitated overnight at 4° C.

This is then centrifuged for 20 min at 15 300×g, 4° C. The pellet is rinsed with a few ml of 2M LiCl. The pellet is resuspended in 5 ml water and transferred to a centrifuge tube. 8M LiCl is added to a final concentration of 2M LiCl and the RNA is precipitated for 3 hr at 4° C. The RNA is pelleted by centrifugation for 20 min at 12 100×g, 4° C. The pellet is rinsed with 2M LiCl and resuspended in 2 ml water. 200 μl 3M Na-acetate and 5.5 ml 100% ethanol are added and the RNA precipitated at −20° C. overnight.

The RNA is pelleted for 15 min at 17 700×g, 4° C. The pellet is dried and resuspended in 1 ml water.

The RNA concentration is calculated and purity assessed in a 1:100 dilution of the stock using the absorbance at 260 nm, 280 nm, 230 nm and 320 nm. The pH is adjusted with conc. $Na_2HPO_4$ to 1 mM before reading.

Approximately 1 μg from each sample is separated on an agarose gel to determine the extent of detectable DNA contamination and RNA degradation. The samples are stored at −70° C.

4.1.2 $1^{st}$ Strand cDNA Synthesis mRNA is isolated from 4 μg total RNA using paramagnetic beads (DYNAL A.S., Oslo, Norway) according to the manufacturer's instructions.

20 μl water is added to each sample and the mRNA is eluted from the beads at 65° C. for 2 min. The supernatant is collected in a new tube and the elution is repeated. The two eluates are pooled.

1 μl Oligo dT$_{(12-18)}$ (500 ng), 5 μl (from ≧1 μg total RNA) mRNA and water to 12 μl are mixed together. The mixture is heated to 70° C. for 10 min, chilled immediately on ice and centrifuged briefly to remove the condensed solution from the tube walls. 4 μl First Strand Buffer (250 mM Tris-HCl, pH 8.3, 375 mM KCl and 15 mM MgCl$_2$), 2 μl 0.1 mM dithiothreitol and 1 μl dNTP mix (10 mM each of DATP, dCTP, dGTP and dTTP) are added. This is mixed gently and incubated for 2 min at 37° C. 1 μl (200 U) reverse transcriptase i.e. Superscript is added and incubated for 1 hr at 37° C. The tubes are then placed on ice.

4.1.3 2$^{nd}$ (Complementary) Strand cDNA Synthesis 91.8 μl water, 32 μl 2$^{nd}$ strand buffer (100 mM Tris-HCl, pH 7.5, 500 mM KCl, 25 mM MgCl$_2$, 0.25 mg/ml Bovine Serum Albumin and 500 mm (NH$_4$)$_2$SO$_4$, 3 μl dNTP mix, 6 μl 0.1M dithiothreitol, 2 μl *E.coli* DNA Ligase (10 U/μl), 4 μl *E.coli* DNA Polymerase (10 U/μl) and 0.7 μl *E.coli* RNase H (1 U/μl) are added to the samples. This is incubated for 2 hr at 16° C. and then 2 μl T4 DNA Polymerase (10 U)/μg is added. This is incubated for a further 5 min at 16° C.

This is then extracted once with 1 vol. of water-saturated phenol and then once with 0.5 vol. phenol and 0.5 vol. chloroform:isoamylalcohol (39:1). 3M Na-Acetate, pH 5.2 is added to a final concentration of 0.3M and mixed gently.

2.5 volumes of 96% Ethanol (−20° C.) is added and the mixture is centrifuged at 10 000×g, 4° C. for 30 min.

The supernatant is discarded and 100 μl 75% Ethanol (−20° C.) is added to the pellet. This mixture is centrifuged at 10 000×g, at 4° C. for 5 min. The supernatant is discarded and the pellet is maintained at room temperature until dry. The pellet is then resuspended in 15 μl water.

4.1.4 Adapter Annealing 5 pmol/μl each of the two TaqI adapters and the two AseI adapters are pre-mixed.

```
TaqI adapter 1:  GACGATGAGTCCGAC       (SEQ ID NO: 1)
TaqI adapter 2:  CGGTCAGGACTCAT        (SEQ ID NO: 2)
AseI adapter 1:  CTCGTAGACTGCGTACC     (SEQ ID NO: 3)
AseI adapter 2:  TAGGTACGCAGTC         (SEQ ID NO: 4)
```

The mixture is heated for 2 min at 70° C. and cooled down slowly to 30° C.

4.1.5 Ligation of Adapters to the cDNA

The two samples of cDNA (prepared according to step 4.1.3, above) are digested with TaqI and AseI. 15 μl of the sample is mixed with 3 μl buffer (50 mM Tris-HCl, pH 7.9, 10 mM MgCl$_2$, 50 mM NaCl, 1 mM Dithiothreitol), 0.3 μl Bovine Serum Albumin (10 mg/ml), 1 μl AseI (10 U) and 1 μl TaqI$^\alpha$ (10 U) The mixture is incubated at 37° C. for at least 2 hr.

The condensate is spun down and incubated at 65° C. for at least 1.5 hr. 1 μl AseI adapter (5 pmol), 1 μl TaqI adapter (50 pmol), 4 μl Ligase buffer (50 mM Tris-HCl, pH 7.8, 10 mM MgCl2, 10 mM Dithiothreitol and 25 g/ml Bovine Serum Albumin), 3 μl water and 1 μl T4 DNA Ligase (1 U) is added. This is incubated at 37° C. for 3 hr. The mixture is then diluted to 500 μl with TE, 8.0 (10 mM Tris, pH 8.0, 1 mM EDTA).

4.1.6 Preamplification

5 μl samples from the previous step are each mixed with 2.5 μl amplification buffer (0.1M Tris-HCl, pH 8.3, 0.5M KCl, 15 mM MgCl$_2$ and 0.1% (w/v) gelatin), 1 μl (5 ng) AseI preamplification primer,1 μl (30 ng) TaqI preamplification primer, 1 μl dNTP mix, 13.5 μl water and 1 μl (1 U) TaqI DNA Polymerase.

```
AseI preamplification primer:  CTCGTAGACTGCGTACCTAAT  (SEQ ID NO: 5)
TaqI preamplification primer:  GACGATGAGTCCTGACCGA    (SEQ ID NO: 6)
```

A temperature cycle of 94° C. for 30 sec, 56° C. for 30 sec and 72° C. for 1 min is run for 25 cycles.

4.1.7 Amplification

5 μl of the samples from the preamplification step are each mixed with 1 μl AseI primer (5 ng ), 1 μl TaqI primer (30 ng), 0.2 μl Taq Polymerase (1 U), 4 μl amplification buffer, 0.4 μl dNTP mix and 8.4 μl water. The primers are end labelled with γ$^{32}$P-ATP.

```
AseI amplification primer:  GACTGCGTACCTAATNN   (SEQ ID NO: 7)
TaqI amplification primer:  GATGAGTCCTGACCGANN  (SEQ ID NO: 8)

(N denotes any of the four deoxynucleotides)
```

A temperature cycle is run of 0.7° reduction in the first step for the first 11 cycles starting at 65° for 30 sec. 72° C. for 1 min and 94° C. for 30 sec. After the initial 11 cycles the cycling is continued for an additional 23 cycles with 65° C. for 30 sec 72° C. for 1 min and 94° C. for 30 sec. The samples are stored at 4° C.

4.1.8 Differential Display

A 6% sequencing type polyacrylamide gel is poured and the sequencing gel apparatus set up. The gel is pre-run until it has achieved 55° C.

5 μl of each sample is mixed with 5 μl sequencing sample dye (95% Formamide, 20 mM EDTA, 0.05% Bromophenol Blue and 0.05% Xylene Cyanol FF). The samples are heated at 75°–80° C. for 2 min and immediately loaded onto the gel. The samples are positioned close to each other on the gel.

The gel is run at 55° C. until the Xylene Cyanol FF band has eluted out. The gel is dried and an autoradiogram is positioned on top of the gel. The film is exposed overnight in darkness. Both the film and dry gel are marked to make it possible to obtain an exact fit for subsequent procedures. The film is developed.

4.1.9 Selecting Differentially Expressed cDNA Clones as Probes

The pattern between the two samples (normal and diseased) are compared and samples are selected that are clearly present in one of the samples but not in the other. The film is positioned precisely on the dried gel. The gel slice corresponding to a selected fragment (which represents a transcript) on the film is cut out and collected in a tube by the addition of 2 µl water to a tube and 0.5 µl water to each selected gel fragment within the cutting lines and use of a scalpel to scrape the fragment up and transfer the fragment to the tube. Between one and ten fragments from each reaction with a specific primer may be collected in this way. Since both of the nucleotides marked N on each of the amplification primers may be one of four possible nucleotides there are $4^4$ or 256 possible combinations that can be used in the amplification. Since one to 10 fragments may be picked from any individual amplification using only a single primer, in total between 256 and 2560 fragments may be picked from a sample using all permutations of the amplification primer.

A temperature cycle is run as before using the unlabelled amplification primers except that the concentration of the primers is increased to 1 µM and the dNTP mix to 200 µM and 40 cycles are performed.

30 ng of the amplified fragments (probes) are applied to a Hybond N filter using a dot blot apparatus. At least two replicas of the filter are produced. The DNA is fixed to the filter by UV crosslinking.

4.1.10 Hybridization of Test Sample cDNA to Filter with Probe cDNA

The second aliquot of leaves from the plants with the diagnosed disease and the healthy plants are used to isolate RNA as described previously. First strand cDNA is prepared as described previously with the exception that 5 µl of [$^{32}$P]αdCTP (spec.activity=10 mCi/ml),is added instead of 5 µl water to create the labelled sample DNA.

The filter is pre-hybridized in a solution of 4.8×SSC (4.2% (w/v) NaCl, 2.1% (w/v) Na-Citrate, pH 7.0), 1×Denhardt (0.02% (w/v) Ficoll 400, 0.02% (w/v) polyvinylpyrrolidone 40, 0.02% (w/v) Bovine Serum Albumin, Fraction V), 50% (w/v) Formatted, 0.2M Tris-HCl, pH 7.6, 5% (w/v) dextran sulfate, 0.1% Na-dodecylsulfate at 42° C. for at least 2 hr in a hybridization oven. The labelled sample DNA is boiled for 3 min and immediately added to the prehybridization solution. This is incubated at 42° C. in the hybridization oven for at least 6 hr or overnight.

The filter is then washed 2× in 2×SSC, 0.1% SDS, 50° C., 10 min, then washed 2× in 1×SSC, 0.1% SDS, 50° C., 15 min, then washed 2× min 0.1×SSC, 0.1% SDS, 50° C., 30 min. The film is exposed in an Instant Imager.

4.1.11 Creating the Standard

One of the signals (resulting from binding of one sample to one of the probes hybridized to the filter) is considered the standard. The ratio for all the other signals on the filter are determined relative this standard signal.

The ratios of the corresponding signals between the plants with the disease and those without the same disease are compared.

Results

Figure 1:
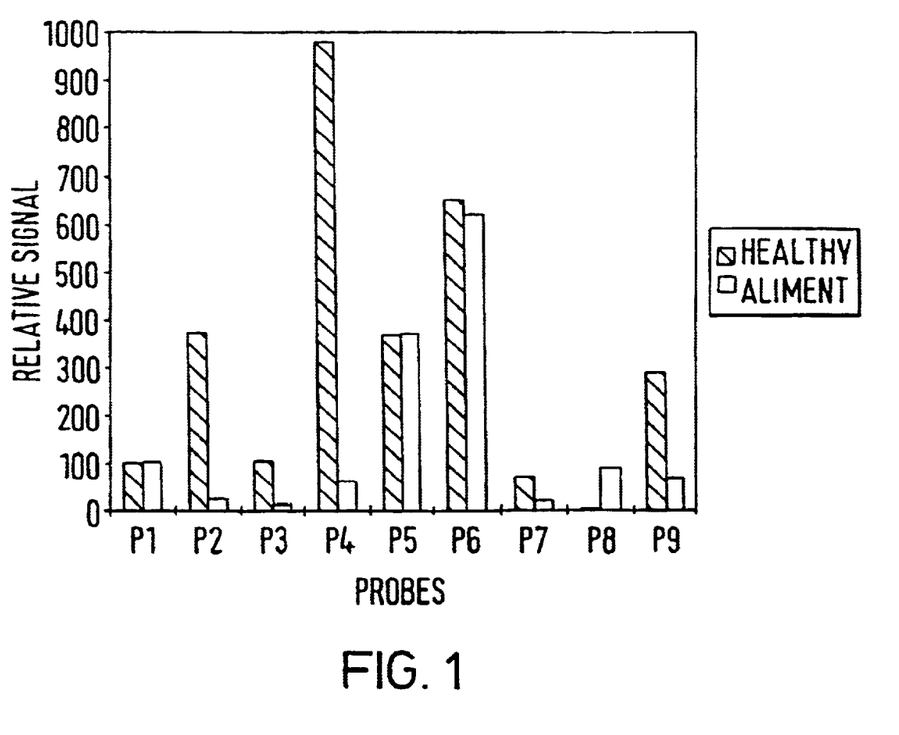
FIG. 1 shows a standard diagnostic gene expression pattern in graphical form for a disease in Arabidopsis.

The results are shown in FIG. 1 for 9 selected cDNAs are shown. P1 has been used as the standard. "Healthy" refers to the sample from the healthy plants and "Ailment" refers to the sample from the plants with the disease in question.

4.2 Applying the Developed Method on an Undiagnosed Plant

A leaf sample of 2 g is collected from the plant under study and immediately frozen in two 1 g aliquots. RNA is extracted as previously described from one of the aliquots. $1^{st}$ strand cDNA is synthesized as previously described and labelled by including [$^{32}$P]αdCTP in the synthesis.

The labelled sample is hybridized to a filter carrying the selected cDNA probes, washed and the signals detected on an Instant Imager as previously described.

The pattern of relative signals from the different probes on the filter is compared with the patterns from the healthy plants and the plants with the disease and a diagnosis for the presence or absence of this disease in the new plant is made.

Example 5

Diagnosis of Disease/Condition in Humans

The diagnosis may be divided in two steps:
  Development of a reproducible expression pattern (fingerprint) typical for the disease/condition to be diagnosed.
  Applying the developed method to a sample from a patient and comparing the expression pattern to patterns developed for the disease/condition.

5.1 Development of a Reproducible Expression Pattern Typical for the Disease/Condition to be Diagnosed 5.1.1 Extraction of Total RNA from Blood 10 ml of blood is collected from a patient who has been diagnosed with the disease of interest and from a patient without this disease but otherwise as similar as possible with regard to age, sex and other factors that may influence the result. Each sample is divided into two aliquots which are immediately frozen in liquid nitrogen.

Using one aliquot of each sample, after thawing the aliquots are centrifuged at 10,000×g for 5 min to pellet the cells. The pellets are resuspended in 1 ml Solution A (4M Guanidine thiocyanate, 25 mM Na-citrate, pH 7.0, 0.5% (w/v) N-laurylsarcosine, 0.1M 2-Mercaptethanol) and the lysate passed through a pipette 7–10 times. 0.1 ml 2M Na-Acetate, pH 4 is added and mixed thoroughly by inversion. 1 ml water-saturated phenol is added and mixed thoroughly. 0.2 ml of 49:1 chloroform/bromochloropropane is added and mixed thoroughly and incubated for 15 min at 0° C. to 4° C. This mixture is centrifuged for 20 min at 10,000×g and the upper aqueous phase is transferred to a clean tube.

The RNA is precipitated by adding 1 ml (1 vol) of 100% isopropanol and the samples are incubated for 30 min at −20° C., followed by centrifugation for 10 min at 10,000×g, 4° C.

The RNA pellet is dissolved in 0.3 ml Solution A. The RNA is then precipitated with 0.3 ml (1 vol) of 100% isopropanol at −20° C. for 30 min. This is centrifuged for 10 min at 10,000×g, 4° C. and the supernatant is discarded.

The RNA pellet is resuspended in 75% Ethanol, vortexed, and incubated for 10–15 min at room temperature. This is centrifuged for 5 min at 10,000×g, 4° C., and the supernatant is discarded. The pellet is dried at room temperature, approximately 10–15 min. The pellet is resuspended in 100 µl water and incubated for 10 to 15 min at 55° to 60° C.

The RNA concentration is calculated and purity assessed in a 1:100 dilution of the stock using the absorbance at 260 nm, 280 nm, 230 nm and 320 nm. The pH is adjusted with conc. $Na_2HPO_4$ to 1 mM before reading.

Approximately 1 µg from each sample is separated on an agarose gel to determine the extent of detectable DNA contamination and RNA degradation. The samples are stored at −70° C.

5.1.2 $1^{st}$ Strand cDNA Synthesis to Selection of Differentially Expressed cDNA Clones as Probes These steps are performed as described in paragraphs 4.1.2 to 4.1.9 above.

5.1.3 Hybridization of Test Sample cDNA to Filter with Probe cDNA

The second aliquot of blood from the normal and diseased patients is used to isolate RNA, prepare labelled first strand cDNA, perform hybridization to the filter carrying the probes and expose the film as described in paragraph 4.1.10.

5.1.4 Creating the Standard

The results are standardized relative to a single signal as described in 4.1.11 above.

The ratios of the corresponding signals between the patient with the disease and the patient without the same disease are compared.

Results

Similar results are obtained to those illustrated in FIG. 1.

5.2 Applying the Developed Method on an Undiagnosed Patient

A blood sample of 2 ml is collected from the patient and immediately frozen in two 1 ml aliquots. RNA is extracted as previously described from one of the aliquots after thawing. $1^{st}$ strand cDNA is synthesized as previously described and labelled by including $[^{32}P]\alpha dCTP$ in the synthesis.

The labelled sample is hybridized to a filter carrying the selected cDNA probes, washed and the signals detected on an Instant Imager as previously described.

The pattern of relative signals from the different probes on the filter is compared with the patterns from the healthy patient and the patient with the disease and a diagnosis for the presence or absence of this disease in the new patient is made.

Example 6

Different Relative Expression Pattern of 7 Selected Probes Found in Roots of Norway Spruce (*Picea abies*) Challenged with Different Types of Stress Methods 1. Seven different informative cDNA probes were attached to a nylon membrane. Most of the clones were isolated from a subtracted cDNA library of Norway spruce roots infected with the fungal pathogen *Pythium dimorphum* (in accordance with the method described in Example 4), whereas others were isolated by similar methods from Norway spruce challenged with other types of stress. The subtracted library was prepared according to the method described in Lönneborg et al. (1995), PCR Meth. Applic., 4, pS168–S177. It was known that all of these clones were induced by at least one type of stress.

2. Norway spruce were grown for 2 months in a growth chamber with a day/night cycle of 12 hr/12 hr light intensity of 500 $\mu$moles×m$^{-2}$×sec$^{-1}$, watering with optimal nutrition once every day. The plants were then challenged either with the nutrition as before (control), maltose media, 24 mg (fresh weight) *Pythium dimorphum*, or 24 mg (fresh weight) Rhizoctonia sp. The plants were challenged for 4 and 8 days. After challenge the roots and upper part were immediately frozen.

3. The remaining steps 4 to 10 were performed essentially as described in Example 4.

4. RNA was extracted from the roots and upper parts and checked for quality and yield.

5. First and second strand cDNA was synthesized using a polyT primer and a primer based on the presence of a 5' cap. In this way only full-length clones were synthesized avoiding the risk of biased synthesis due to multiple priming sites.

6. All cDNA was amplified using the PCR technique and using the same set of primers.

7. The cDNA pool was labelled using the polyT primer.

8. Filters, each carrying the 7 probes, were pre-hybridized at 65° C. for 6 hours and the labelled cDNA samples were added to one filter each and the immobilized filters were allowed to hybridize overnight at 65° C.

9. The filters were washed to remove any non-specifically hybridized label.

10. The radioactive signals of the individual probes on each filter were counted using an Instant Imager and the relative signals calculated.

Results

The pattern created for the filters with roots from control (day 4), maltose (day 4 and 8), *Pythium dimorphum* (day 4 and 8), Rhizotonia sp. (day 4) and needles from control (day 4) and *Pythium dimorphum* (day 4) are presented in FIG. 2. For maltose at day 4, two independent duplicates were performed which indicated the reproducibility of the experiment.

Figure 2:
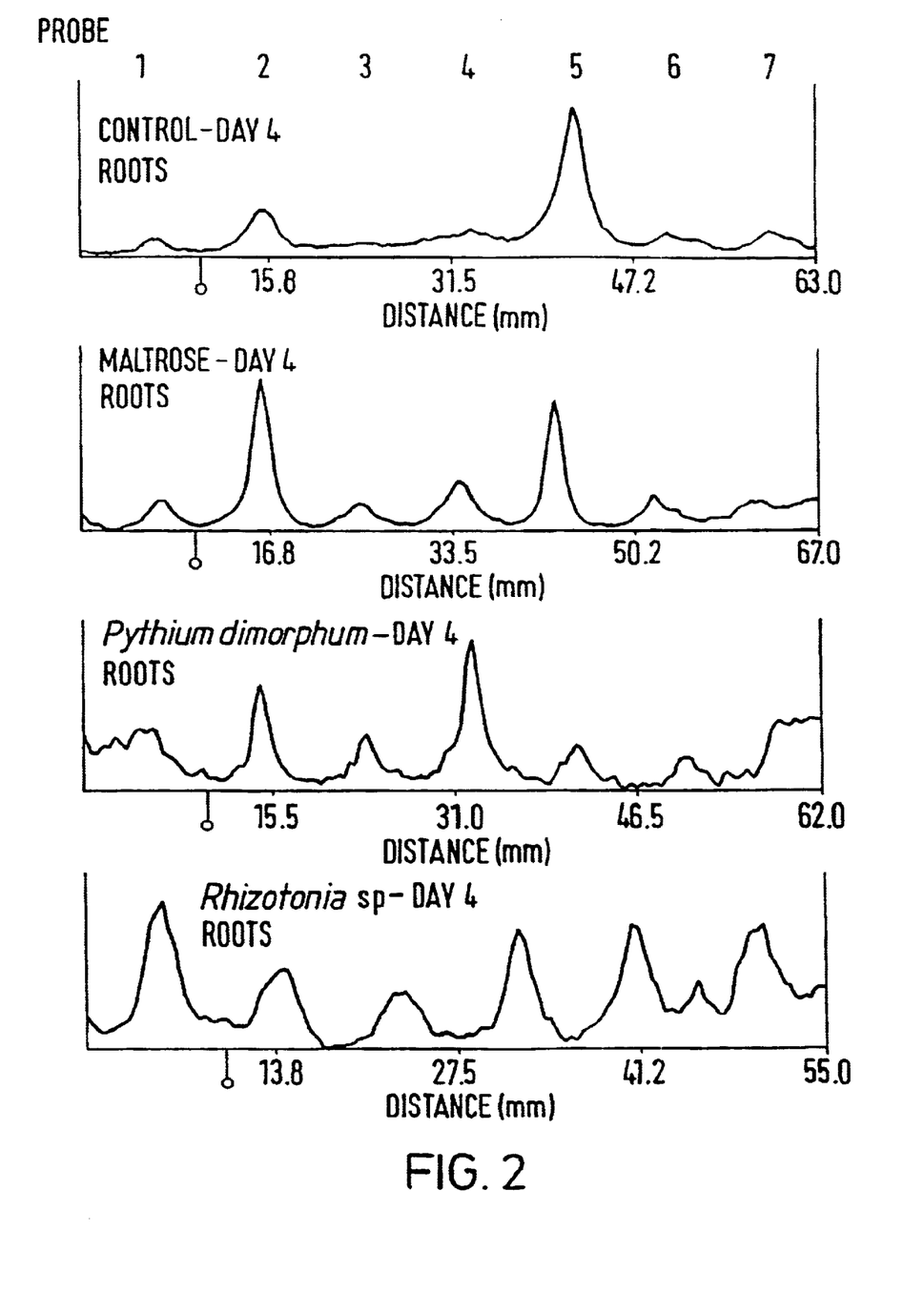
FIG. 2 shows the extent of binding of cDNA isolated from *Picea abies* challenged with different types of stress to 7 different probes.

The results show that each of these challenges creates distinct patterns using this set of probes. It can also be seen that the stresses induce the plants systemically allowing use of different parts of the plants for assay. Furthermore, the differential expression of particular transcripts at different stages of the stress may also be seen.

What is claimed is:

1. A method of obtaining isolated selected mRNA species or isolated selected cDNA species useful for diagnosing or identifying Alzheimer's disease or stage thereof in a human comprising the steps of:

(a) isolating mRNA from cells of one or more humans which are known to have said disease or a stage thereof (diseased sample), wherein said cells are obtained from blood, wherein the resulting isolated mRNA is optionally subjected to reverse transcription to obtain isolated cDNA;

(b) isolating mRNA from corresponding cells of one or more normal humans (normal sample), wherein the resulting isolated mRNA is optionally subjected to reverse transcription to obtain isolated cDNA;

(c) separating, by a non-sequence based separation technique, mRNA species or cDNA species present within each of the resulting isolated mRNA or isolated cDNA of step (a) and step (b), wherein the resulting separated mRNA species are optionally subject to reverse transcription to obtain separated cDNA species;

(d) selecting two or more mRNA species or two or more cDNA species from the resulting separated mRNA species or resulting separated cDNA species obtained in step (c), respectively, which are present at a different level in the normal sample than in the diseased sample by identifying a signal corresponding to each mRNA species or cDNA species, wherein the resulting selected two or more mRNA species are optionally subjected to reverse transcription to obtain two or more selected cDNA species; and (e) isolating the resulting two or more selected mRNA species or resulting two or more selected cDNA species obtained in step (d) to obtain isolated selected mRNA species or isolated selected cDNA species, wherein the resulting isolated selected mRNA species are optionally subjected to reverse transcription to obtain isolated selected cDNA species.

2. The method as claimed in claim 1, wherein in steps (a) and (b), the resulting isolated mRNA is subjected to reverse transcription to obtain isolated cDNA.

3. The method as claimed in claim 2, wherein said isolated cDNA is amplified.

4. The method as claimed in claim 1, wherein said isolated cDNA is labelled.

5. The method as claimed in claim 1, wherein, in step (e), between 50 and 100 mRNA species or cDNA species are isolated and selected.

6. The method as claimed in claim 1, wherein, in step (e), between 10 and 500 mRNA species or cDNA species are isolated and selected.

7. The method as claimed in claim 1, wherein, in step (c), said separation technique is gel electrophoresis.

8. A method of preparing a gene transcript pattern probe kit comprising the steps of:

(a) isolating mRNA from cells of one or more humans which are known to have Alzheimer's disease or a stage thereof (diseased sample), wherein said cells are obtained from blood, wherein the resulting isolated mRNA is optionally subjected to reverse transcription to obtain isolated cDNA;

(b) isolating mRNA from corresponding cells of one or more normal humans (normal sample), wherein the resulting isolated mRNA is optionally subjected to reverse transcription to obtain isolated cDNA;

(c) separating, by a non-sequence based separation technique, mRNA species or cDNA species present within each of the resulting isolated mRNA or isolated cDNA of step (a) and step (b), wherein the resulting separated mRNA species are optionally subject to reverse transcription to obtain separated cDNA species;

(d) selecting two or more mRNA species or two or more cDNA species from the resulting separated mRNA species or resulting separated cDNA species obtained in step (c), respectively, which are present at a different level in the normal sample than in the diseased sample by identifying a signal corresponding to each mRNA species or cDNA species, wherein the resulting selected two or more mRNA species are optionally subjected to reverse transcription to obtain two or more selected cDNA species;

(e) isolating the resulting two or more selected mRNA species or resulting two or more selected cDNA species obtained in step (d) to obtain isolated selected mRNA species or isolated selected cDNA species, wherein the resulting isolated selected mRNA species are optionally subjected to reverse transcription to obtain isolated selected cDNA species; and (f) immobilizing the resulting isolated selected mRNA species or isolated selected cDNA species of step (e) on at least one solid support so as to form a gene transcript pattern probe kit.

9. The method as claimed in claim 8, wherein, prior to immobilizing in step (f), the resulting isolated selected mRNA species or isolated selected cDNA species of step (e) are amplified.

10. The method as claimed in claim 8, wherein said solid support is a filter.

11. A method of preparing a standard gene transcript pattern characteristic of Alzheimer's disease or stage thereof comprising the steps of:

(a) isolating mRNA from cells of one or more humans known to have said disease or a stage thereof, wherein said cells are obtained from blood, wherein the resulting isolated mRNA is optionally subjected to reverse transcription to obtain isolated cDNA;

(b) hybridizing the resulting isolated mRNA or isolated cDNA of step (a) to two or more mRNA species which are present at a different level in cells in a normal sample than corresponding cells in an Alzheimer's diseased sample, wherein the two or more mRNA species or cDNA species are specific for said disease or stage thereof and wherein said cells are obtained from human blood, or to two or more cDNA species transcribed from said mRNA species, wherein said mRNA or cDNA species are immobilized on a solid support; and (c) assessing the amount of hybridisation so as to obtain said standard gene transcript pattern.

12. A method of preparing a test gene transcript pattern for Alzheimer's disease or stage thereof comprising the steps of:

(a) isolating mRNA from cells of a test human, wherein said cells are obtained from blood, wherein the resulting isolated mRNA is optionally subjected to reverse transcription to obtain isolated cDNA;

(b) hybridizing the resulting isolated mRNA or isolated cDNA of step (a) to two or more mRNA species which are present at a different level in cells in a normal sample than corresponding cells in an Alzheimer's diseased sample, wherein the two or more mRNA species or cDNA species are specific for said disease or stage thereof and wherein said cells are obtained from human blood, or to two or more cDNA species transcribed from said mRNA species, wherein said mRNA or cDNA species are immobilized on a solid support; and (c) assessing the amount of hybridization so as to obtain said test gene transcript pattern.

13. A method of diagnosing or identifying Alzheimer's disease or stage thereof in a test human comprising the steps of:

(a) isolating mRNA from cells of a test human, wherein said cells are obtained from blood, wherein the resulting isolated mRNA is optionally subjected to reverse transcription to obtain isolated cDNA;

(b) hybridizing the resulting isolated mRNA or isolated cDNA of step (a) to two or more mRNA species which are present at a different level in cells in a normal sample than corresponding cells in an Alzheimer's diseased sample, wherein the two or more mRNA species or cDNA species are specific for said disease or stage thereof and are obtained from human blood, or to two or more cDNA species transcribed from said mRNA species, wherein said mRNA or cDNA species are immobilized on a solid support;

(c) assessing the amount of hybridization so as to obtain a hybridization pattern;

(d) comparing the resulting hybridization pattern obtained in step (c) with a hybridization pattern obtained by hybridizing isolated mRNA or isolated cDNA prepared from corresponding cells from one or more humans known to have said disease or stage thereof to the two or more mRNA species or two or more cDNA species transcribed from said RNA species, wherein said mRNA species or cDNA species are immobilized on a solid support; and (e) assessing the amount of hybridization, so as to determine the degree of correlation indicative of the presence of said disease or stage thereof, and so as to diagnose or identify said disease or a stage thereof in said test human.

* * * * *